(12) United States Patent
Fisher et al.

(10) Patent No.: US 7,285,897 B2
(45) Date of Patent: Oct. 23, 2007

(54) CURVED MICROMACHINED ULTRASONIC TRANSDUCER ARRAYS AND RELATED METHODS OF MANUFACTURE

(75) Inventors: Rayette A. Fisher, Niskayuna, NY (US); David M. Mills, Niskayuna, NY (US); Lowell Scott Smith, Niskayuna, NY (US); Robert S. Lewandowski, Amsterdam, NY (US)

(73) Assignee: General Electric Company, Schenectady, NY (US)

( * ) Notice: Subject to any disclaimer, the term of this patent is extended or adjusted under 35 U.S.C. 154(b) by 690 days.

(21) Appl. No.: 10/749,645

(22) Filed: Dec. 31, 2003

(65) Prior Publication Data

US 2005/0146247 A1    Jul. 7, 2005

(51) Int. Cl.
*H01L 41/08* (2006.01)
(52) U.S. Cl. ..................................... 310/334
(58) Field of Classification Search ............... 310/309, 310/330, 334–335, 311, 326–327, 329, 337, 310/328, 322, 325; 73/642; 600/459; *H01L 41/08*
See application file for complete search history.

(56) References Cited

U.S. PATENT DOCUMENTS

| 5,109,860 | A | * | 5/1992 | Gelly et al. | 600/459 |
| 5,423,220 | A | * | 6/1995 | Finsterwald et al. | 310/322 |
| 5,637,800 | A | | 6/1997 | Finsterwald et al. | 73/642 |
| 6,659,954 | B2 | * | 12/2003 | Robinson | 600/459 |
| 7,030,536 | B2 | * | 4/2006 | Smith et al. | 310/309 |

OTHER PUBLICATIONS

Jin et al., "Micromachined Capacitive Transducer Arrays for Medical Ultrasoind Imaging", 1998 IEEE Ultrasonics Symposium, pp. 1877-1880.
Ladabaum et al., "Surface Micromachined Capacitive Ultrasonic Transducers", IEEE Trans. Ultrasonics, Ferroelectrics, and Frequency Control, vol. 45, No. 3 (May 1998), pp. 678-690.

* cited by examiner

*Primary Examiner*—Darren Schuberg
*Assistant Examiner*—Karen Beth Addison
(74) *Attorney, Agent, or Firm*—Fletcher Yoder (57) ABSTRACT

A curved sensor device, such as an ultrasonic transducer array, is fabricated from a flat micromachined sensor (such as cMUT or pMUT) array constructed using micromachined electromechanical systems (MEMS) techniques. The device comprises: a support structure comprising a spine having a profile that is generally curved and a multiplicity of teeth extending from one side of the curved spine; and a multiplicity of sensors built on the support structure. The spine can be bent forward or backward and attached to a curved front face of a support member, thereby causing the sensors to adopt a curved array.

28 Claims, 3 Drawing Sheets

CURVED MICROMACHINED ULTRASONIC TRANSDUCER ARRAYS AND RELATED METHODS OF MANUFACTURE

BACKGROUND OF THE INVENTION

This invention generally relates to arrays of micromachined sensors, including but not limited to micromachined ultrasonic transducers (MUTs). One specific application for MUTs is in medical diagnostic ultrasound imaging systems. Another specific example is for non-destructive evaluation (NDE) of materials, such as castings, forgings, or pipelines. However, the curved sensor arrays disclosed herein are not limited to ultrasound transducers, but rather may also comprise, e.g., temperature, pressure, or optical sensors.

Conventional ultrasound imaging systems comprise an array of ultrasonic transducers that are used to transmit an ultrasound beam and then receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is dynamically focused at a succession of ranges along the scan line as the reflected ultrasonic waves are received.

For ultrasound imaging, the array typically has a multiplicity of transducers arranged in one or more rows and driven with separate voltages. By selecting the time delay (or phase) and amplitude of the applied voltages, the individual transducers in a given row can be controlled to produce ultrasonic waves that combine to form a net ultrasonic wave that travels along a preferred vector direction and is focused in a selected zone along the beam.

The same principles apply when the transducer probe is employed to receive the reflected sound in a receive mode. The voltages produced at the receiving transducers are summed so that the net signal is indicative of the ultrasound reflected from a single focal zone in the object. As with the transmission mode, this focused reception of the ultrasonic energy is achieved by imparting separate time delay (and/or phase shifts) and gains to the signal from each receiving transducer. The time delays are adjusted with increasing depth of the returned signal to provide dynamic focusing on receive.

The quality or resolution of the image formed is partly a function of the number of transducers that respectively constitute the transmit and receive apertures of the transducer array. Accordingly, to achieve high image quality, a large number of transducers, referred to herein as elements, is desirable for both two- and three-dimensional imaging applications. The ultrasound elements are typically located in a hand-held transducer probe that is connected by a flexible cable to an electronics unit that processes the transducer signals and generates ultrasound images. The transducer probe may contain both ultrasound transmit circuitry and ultrasound receive circuitry.

Convex curved ultrasound probes are the dominant choice for abdominal imaging. They provide a large field of view with excellent resolution achieved with a relatively simple system beamformer. Most ultrasound probes are made from piezoelectric ceramics or single crystals. Each piezoelectric element vibrates in the thickness mode as a half-wave resonator. Engineers have managed to widen the bandwidth of these vibrators through an extensive collection of additional impedance matching layers, backings, and electrical tuning techniques.

Curved probes are generally fabricated by laminating piezoelectric ceramic, matching layers, and a backing together as a flat acoustic stack. The stack is subsequently diced (often from the back surface through the backing, ceramic, and part of the matching layers) at a very fine pitch to allow them to easily bend to conform to a curved shape. The resulting structure is then affixed to an appropriately shaped preformed backing block. A typical example is disclosed in U.S. Pat. No. 5,637,800.

It is well known in the art that any surface can be described at a point by two orthogonal radii of curvature, $r_1$ and $r_2$. The requirement that the surface remain continuous is equivalent to requiring the product of the inverses of the two radii of curvature to be a constant:

$$\frac{1}{r_1 r_2} = \text{constant} \qquad (1)$$

Two radii of curvature of a flat plate are both infinite, and the constant is 0. Hence it is easy to curve the array in either the azimuthal or elevational direction, where one inverse radius remains 0. However, curvature in both directions is severely limited.

Recently semiconductor processes have been used to manufacture ultrasonic transducers of a type known as micromachined ultrasonic transducers (MUTs), which may be of the capacitive (cMUT) or piezoelectric (pMUT) variety. cMUTs are tiny diaphragm-like devices with electrodes that convert the sound vibration of a received ultrasound signal into a modulated capacitance. For transmission the capacitive charge is modulated to vibrate the diaphragm of the device and thereby transmit a sound wave. pMUTs are similar except that the diaphragm is bimorphic, consisting of a piezoelectric and an inert material like silicon nitride or silicon. The bimorphic diaphragm typically has greater sensitivity but lower bandwidth properties.

One advantage of MUTs is that they can be made using semiconductor fabrication processes, such as microfabrication processes grouped under the heading "micromachining". As explained in U.S. Pat. No. 6,359,367:

Micromachining is the formation of microscopic structures using a combination or subset of (A) Patterning tools (generally lithography such as projection-aligners or wafer-steppers), and (B) Deposition tools such as PVD (physical vapor deposition), CVD (chemical vapor deposition), LPCVD (low-pressure chemical vapor deposition), PECVD (plasma chemical vapor deposition), and (C) Etching tools such as wet-chemical etching, plasma-etching, ion-milling, sputter-etching or laser-etching. Micromachining is typically performed on substrates or wafers made of silicon, glass, sapphire or ceramic. Such substrates or wafers are generally very flat and smooth and have lateral dimensions in inches. They are usually processed as groups in cassettes as they travel from process tool to process tool. Each substrate can advantageously (but not necessarily) incorporate numerous copies of the product. There are two generic types of micromachining . . . 1) Bulk micromachining wherein the wafer or substrate has large portions of its thickness sculptured, and 2) Surface micromachining wherein the sculpturing is generally limited to the surface, and particularly to thin deposited films on the surface. The micromachining definition used herein includes the use of conventional or known micromachinable materials including silicon, sapphire, glass materials of all types, polymers (such as polyimide), polysilicon, silicon nitride, silicon oxynitride, thin film metals such as aluminum alloys, copper alloys and tungsten, spin-on-glasses (SOGs), implantable or diffused dopants and grown films such as silicon oxides and nitrides.

The same definition of micromachining is adopted herein. The systems resulting from such micromachining processes are typically referred to as "micromachined electromechanical systems (MEMS).

Conventional cMUTs resemble tiny drums (made of silicon nitride or other similar materials, such as silicon) that are "beat" electrostatically. The drumhead vibrates to both emit and receive ultrasonic waves. A cMUT probe consists of an array of many elements, each element comprising a respective plurality of individual cMUT cells that have been hard-wired together.

A typical cMUT cell comprises a thin silicon or silicon nitride membrane with an electrode, suspended over a cavity formed on a silicon substrate. A bottom electrode is formed in or on the silicon substrate or by doping the substrate so that it is conductive. All cMUT cells in an element are electrically connected using top and bottom electrodes. The membrane vibrates to both emit and receive ultrasonic waves. The driving force for the deflection of the membrane during transmit is the electrostatic attraction between the top and bottom electrodes when a voltage is impressed across them. If an alternating voltage drives the membrane, significant ultrasound generation results. Conversely, if the membrane is biased appropriately and subjected to incoming ultrasonic waves, significant detection currents are generated. Typical thicknesses of the membrane lie in the range of 1 to 3 microns and the cavity gap is on the order of 0.1 to 0.3 micron. The lateral dimensions of the cMUT cell range from 10 to 100 microns for cMUT array operating frequencies of 2 to 15 MHz.

Capacitive micromachined ultrasound transducers are fabricated on flat crystalline silicon substrates, and represent a novel approach to ultrasound transduction. Since the micromachined membrane typically oscillates far above the operating frequency of the probe and is damped by the material (such as an acoustic lens) that is applied to the top surface, these devices are inherently broadband. Operating over a wider frequency range than the comparable piezoelectric transducers, these cMUTS should improve B-mode, color flow, and harmonic imaging. However, cMUT ultrasonic probes are usually built on very stiff, hard to bend substrates.

There is a need for methods of making curved cMUT (or PMUT) substrates without diminishing their acoustic performance advantages. In particular, there is a need for a method of making a convex curved cMUT substrate, thereby achieving the wide field of view so many clinicians find appealing in convex curved piezoelectric arrays used in abdominal imaging.

BRIEF DESCRIPTION OF THE INVENTION

The present invention is directed to curved sensor devices comprising an array of micromachined sensors, such as MUTs. In the case of MUTs, such structures provide the performance benefits of the MUT and the system architectural benefits of the curved aperture. The front face of the device be either convex or concave.

One aspect of the invention is an sensor device comprising: a support structure comprising a spine having a profile that is generally curved and a multiplicity of teeth extending from one side of the curved spine; and a multiplicity of sensors built on the support structure and supported in positions whereby a curved aperture is provided.

Another aspect of the invention is an sensor device comprising: a continuous substrate comprising a front face and a multiplicity of spaced plateaus projecting rearward; a multiplicity of sensors built on the front face of the substrate; a multiplicity of backing bodies, each backing body being attached to a rear face of a respective plateau; a support member having a front face, respective rear faces of the backing bodies being attached to the front face of the support member, wherein the sensors do not lie in the same plane.

A further aspect of the invention is an sensor device comprising: a support member having a front face; a continuous layer of backing material comprising a rear face attached to the front face of the support member; a multiplicity of backing bodies connected to and extending forward of the continuous layer of backing material; a multiplicity of sections of a substrate, each substrate section comprising a rear face attached to a front face of a respective backing body, adjacent ones of the substrate sections being separated from each other by a respective acoustically isolating gap or filled space; and a multiplicity of groups of sensors distributed over the front faces of the substrate sections, each group being built on a front face of a respective one of the substrate sections, wherein the sensors do not lie in the same plane.

Yet another aspect of the invention is a method of manufacturing an sensor device, comprising the following steps: (a) micromachining a multiplicity of sensors on a front face of a substrate; (b) attaching a rear face of the substrate to a backing plate to form a lamination; (c) dicing the lamination from the rear through the backing plate and further through a partial thickness of the substrate but not through a level where the sensors reside, forming a multiplicity of teeth separated by kerfs and leaving the sensors undisturbed, the teeth being connected at the roots of the kerfs by thin webs of the substrate; (d) bending the thin webs of the substrate in the same direction, causing the diced lamination to bow one way or the other; and (e) attaching rear faces of the teeth of the bent lamination to a front face of a support member having a profile that is concave or convex.

A further aspect of the invention is a method of manufacturing an sensor device, comprising the following steps: (a) micromachining a multiplicity of sensors on a front face of a substrate in areas not to be diced; (b) attaching a rear face of the substrate to a plate of backing material to form a lamination; (c) dicing the lamination from the front through the substrate in areas where no sensors reside and further through a partial thickness of the backing plate, thereby forming a multiplicity of teeth separated by kerfs, the teeth being connected at the roots of the kerfs by thin webs of the backing material; (d) bending the thin webs of the backing material in the same direction, causing the diced lamination to bow one way or the other; and (e) attaching a rear face of the bowed backing material to a front face of a support member having a profile that is concave or convex.

Other aspects of the invention are disclosed and claimed below.

BRIEF DESCRIPTION OF THE DRAWINGS

Reference will now be made to the drawings in which similar elements in different drawings bear the same reference numerals.

DETAILED DESCRIPTION OF THE INVENTION

The innovation disclosed here is a unique method of making curved MUT arrays. For the purpose of illustration, various embodiments of the invention will be described that utilize capacitive micromachined ultrasonic transducers (cMUTs). However, it should be understood that the aspects of the invention disclosed herein are not limited to use of cMUTs, but rather may also employ pMUTs.

Figure 1:
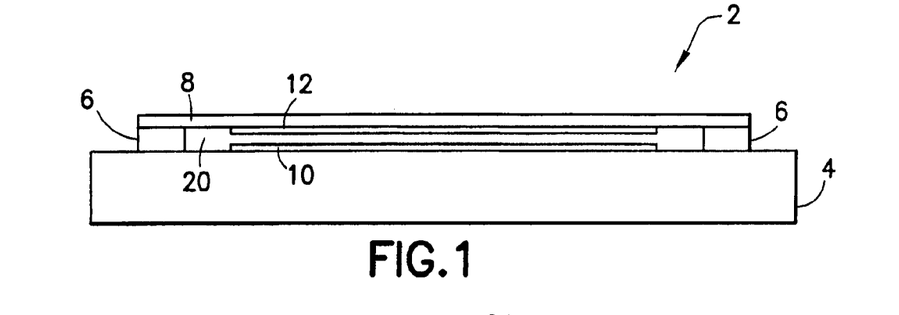
FIG. 1 is a drawing showing a cross-sectional view of a typical cMUT cell.

Capacitive micromachined ultrasound transducers are silicon-based devices that comprise small (e.g., 50 μm) capacitive "drumheads" or cells that can transmit and receive ultrasound energy. Referring to FIG. 1, a typical cMUT cell 2 is shown in cross section. An array of such cMUT transducer cells is typically fabricated on a substrate 4, such as a silicon wafer. For each MUT transducer cell, a thin flexible membrane or diaphragm 8, which may be made of silicon, silicon nitride, or other suitable material, is suspended above the substrate 4. The membrane 8 is supported on its periphery by an insulating support 6, which may be made of silicon oxide or silicon nitride or may be part of the substrate. The insulating support typically comprises a relatively rigid vertical wall that encloses a cavity 20 underneath the membrane 8. One cMUT cell typically shares sections of the wall with its neighbors. The cavity 20 between the membrane 8 and the substrate 4 may be air- or gas-filled or wholly or partially evacuated. A film or layer of conductive material, such as aluminum alloy, gold or other suitable conductive material, forms an electrode 12 on the membrane 8, and another film or layer made of conductive material forms an electrode 10 on the substrate 4. Alternatively, the electrode 10 can be embedded in the substrate 4 or an electrode may be formed by highly doped silicon in the substrate or the membrane. Also the electrode 12 can be on top of membrane 8 rather than on the bottom as shown in FIG. 1 or could even be embedded in the membrane.

The two electrodes 10 and 12, separated by the cavity 20, form a capacitance. When an impinging acoustic signal causes the membrane 8 to vibrate, the variation in the capacitance can be detected using associated electronics (not shown in FIG. 1), thereby transducing the acoustic signal into an electrical signal. Conversely, an AC signal applied to one of the electrodes will modulate the charge on the electrode, which in turn causes a modulation in the capacitive force between the electrodes, the latter causing the diaphragm to move and thereby transmit an acoustic signal.

In operation, the cMUT cell typically has a dc bias voltage $V_{bias}$ that is significantly higher than the time-varying voltage v(t) applied across the electrodes. The bias attracts the top electrode toward the bottom through coulombic force. In this heavily biased case, the cMUT drumheads experience a membrane displacement u given as follows:

$$u(t) \approx \frac{\varepsilon}{d^2} * V_{bias} * v(t) \qquad (2)$$

where d is the distance between the electrodes or plates of the capacitor, and å is the effective dielectric constant of the cell. The sensitivity of the cMUT cell has been found to be the greatest when the bias voltage is high and electrodes are closer together.

Due to the micron-size dimensions of a typical MUT, numerous MUT cells are typically fabricated in close proximity to form a single transducer element. The individual cells can have round, rectangular, hexagonal, or other peripheral shapes. Hexagonal shapes provide dense packing of the MUT cells of a transducer element. The MUT cells can have different dimensions so that the transducer element will have composite characteristics of the different cell sizes, giving the transducer a broadband characteristic. cMUT cells can be electrically connected together in the micromachining process to form elements.

cMUTs and pMUTs are usually formed in a thin layer on the surface of a MEMS substrate. Silicon is by far the most common substrate, although other materials like gallium arsenide, semiconductor hetero-junctions or even ceramics or polymers could be employed for specific applications. Layers on the order of magnitude of a micron are deposited by traditional semiconductor fabrication processes and lithographic techniques are used to create specific patterns. The detailed fabrication of surface micromachined cMUTs is described in several publications. See, e.g., Ladabaum et al., "Surface Micromachined Capacitive Ultrasonic Transducers," IEEE Trans. UFFC, Vol. 45, No. 3, pp. 678-690 (1998); Jin et al., "Micromachined Capacitive Transducer Arrays for Medical Ultrasound Imaging," Proc. IEEE Ultrason. Symp., Sendai, Japan, (1998), pp. 1877-1880; and Jin et al., "The Microfabrication of Capacitive Ultrasonic Transducers," IEEE/ASME J. Microelectromech. Syst., Vol. 7, pp. 295-302, September (1998). In addition recent work has shown how bulk micromachining can also be used to form MUT membranes through wafer bonding.

MUTs are traditionally fabricated on flat silicon wafers. Since a typical MUT fabrication requires many individual processes, the process control of the individual steps is critical. Flat substrates allow for more uniform depositions over wider areas mainly because the instruments are designed to accept flat substrates. It would in principle be possible to perform many of these processes on curved substrates, if the rest of the apparatus was built to have concentric curved surfaces. Thus apparatus components would need to be modified for each different radius. It is therefore unlikely that MUTs will be made on anything except flat substrates in the foreseeable future.

In accordance with several embodiments of the invention disclosed herein, cMUT arrays are fabricated on flat wafers, and subsequently those wafers are bent or bowed to form a curved aperture, convex or concave. Significant differences from the methods used to bend piezoelectric arrays arise due to the very different moduli and fracture toughness of silicon as compared to those of matching layer plastics or piezoceramics.

In one example of a piezoceramic case, two acoustic matching layers are stacked on the top surface of the ceramic. The ceramic and inner matching layer are diced from the back surface leaving a thin web of outer matching layer material holding the device together. This flimsy structure is then carefully bent onto a stiff packing plate where it is adhesively bonded into place. Stresses in the array are restricted to the outer matching layer.

An examination of the bending stresses and the fracture toughness will highlight the difference between making curved piezoelectric versus silicon-based cMUT arrays. Stress $\sigma_z$ in a bending plate is proportional to the modulus of tension and compression (Young's modulus, E) and inversely proportional to the radius of curvature R:

$$\sigma_z = Ex/R \quad (3)$$

where x is the distance in the plate thickness dimension with the origin at the center of the plate. So it is easier to bend materials with low modulus. Table 1 shows the moduli and fracture toughness of several materials used to make ultrasound transducers. Both silicon and piezoceramic are much stiffer than the other transducer materials; silicon has the highest modulus. Fracture toughness is proportional to the force required to break the material from an existing crack. It may be assumed that essentially all materials have microscopic flaws that can initiate further cracking.

TABLE 1

| Material | Modulus (E) - Tension/Compression ($10^{10}$ N/m$^2$) | Modulus - Shear ($10^{10}$ N/m$^2$) | Fracture Toughness (K) (MPa-m$^{1/2}$) |
|---|---|---|---|
| Piezoceramic (PZT) | 14 | 2 | 3-5 |
| Matching Layer (Rexolite) | 0.9 | 0.1 | 1.0 |
| Silicon | 17 | 8 | 0.9 |

In order to estimate the likelihood of fracture, one can examine the stresses near a crack propagating normal to the applied tensile stress:

$$\sigma = \frac{K}{\sqrt{2\pi x}} \quad (4)$$

where K is the fracture toughness and x is the distance from the crack tip. Using the maximum stress that occurs when x is maximum, at the edge of the plate, and equating stresses gives the following relationship for cracking:

$$\frac{E}{2R}\sqrt{t^3\pi} > K \quad (5)$$

where t is the plate thickness. So the figure of merit for bending without breaking at a constant radius is $$\frac{K}{E\sqrt{t^3}} \quad (6)$$

Expressed another way, silicon has to be about seven times thinner than Rexolite, a typical outer matching layer for piezoelectric ceramic, to maintain the same margin against fracture at a constant radius.

In the piezoelectric case, dicing from the back, the PZT structure confines the stress to the matching layer, a comparatively compliant material. Similarly, dicing from the front confines the stresses to the reasonably elastic acoustic backing. For the MUT case, there is nothing in front of the silicon to accept the stress, and a different tactic is needed. For the same structure, the stress can be minimized by minimizing x, i.e., the remaining silicon web, before bending. Moreover, there are significant reasons why dicing of MUTs is undesirable. One of the key advantages of MUT technology is the ease of processing entire arrays of transducer elements using silicon processing without requiring detailed attention to individual elements. Dicing limits the size of underlying electronic circuits and the variety of subsequent semiconductor processes.

Silicon, when thin enough, curls in response to the residual stresses in the wafer. This is especially pronounced when a layer of high tensile strength is applied to one side of the wafer, thereby straining the whole structure. In many cMUT structures, the membrane surface already serves this role so that the curl is inherently in the wrong direction, toward rather than away from the patient, for applications where a broad field of view is desired. It becomes more difficult to apply a layer on the back surface of the wafer to overcome the initial tendency.

Furthermore, it is well known in the art, that fractures are more common when the cracks have sharp edges. Hence it is desirable for the isolating kerfs to have very smooth surfaces and rounded corners. This can be achieved in several ways. Using a diamond saw, the blade can be dressed to have relatively rounded corners. Using laser processing, the diffraction of the beam tends to generate this relatively gentle profile. Finally, relatively isotropic etches can be used in previously created slots to even out otherwise jagged regions. Such isotropic etches are disclosed by M. J. Madou in Section 16.5: Wet Isotropic and Anisotropic Etching, in: The MEMS Handbook, edited by M. Gad-el-Hak, CRC Press, 2002. As disclosed therein, isotropic etchants are usually acidic, such as HF/HNO$_3$/CH$_3$COOH (HNA), and produce rounded isotropic features in single crystalline silicon.

Various embodiments of the invention will now be described. Each disclosed embodiment is an ultrasonic probe comprising a support structure and a multiplicity of MUT cells built on the support structure and supported in positions whereby a curved aperture is provided. The support structure in turn comprises a spine having a profile that is generally curved and a multiplicity of teeth extending from one side of the curved spine. The active face of the probe may have a concave or convex profile. The spine may be formed by an undiced portion of a silicon substrate on which the cMUTs are built or by an undiced portion of a backing layer made of acoustically attenuative material. In the latter case, the cMUTs are disposed on the end faces of the teeth. However, it should be appreciated that sensor devices other than ultrasonic probes fall within the scope of the invention. For example, curved sensor devices comprising arrays of micromachined temperature, pressure or optical sensors can be constructed.

Figure 2:
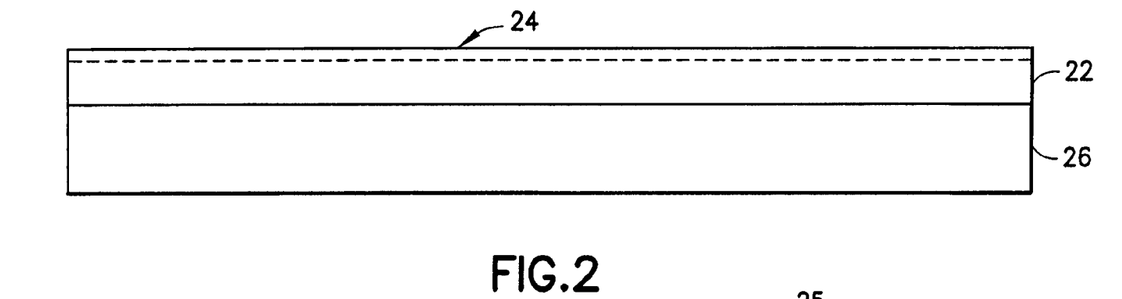
FIG. 2 is a drawing showing a stage in a manufacturing process wherein a cMUT wafer is laminated to a backing plate.
Figure 3:
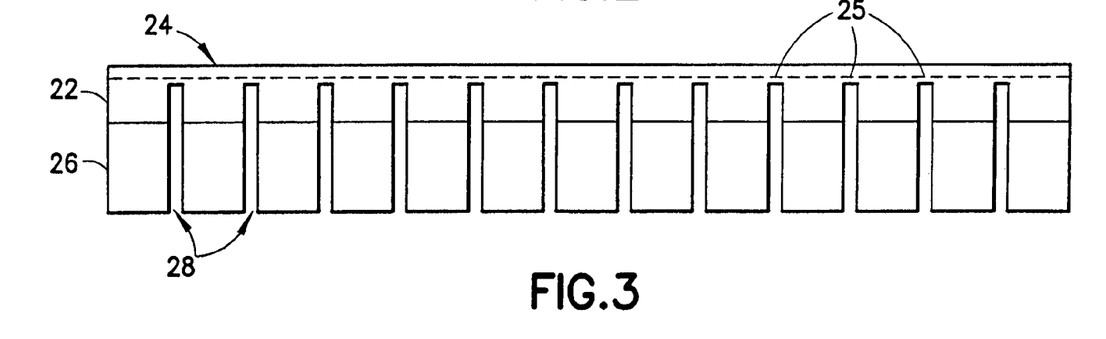
FIG. 3 is a drawing showing a stage in a manufacturing process in accordance with one embodiment of the invention wherein the lamination shown in FIG. 2 has been diced from the rear.
Figures 4, 5:
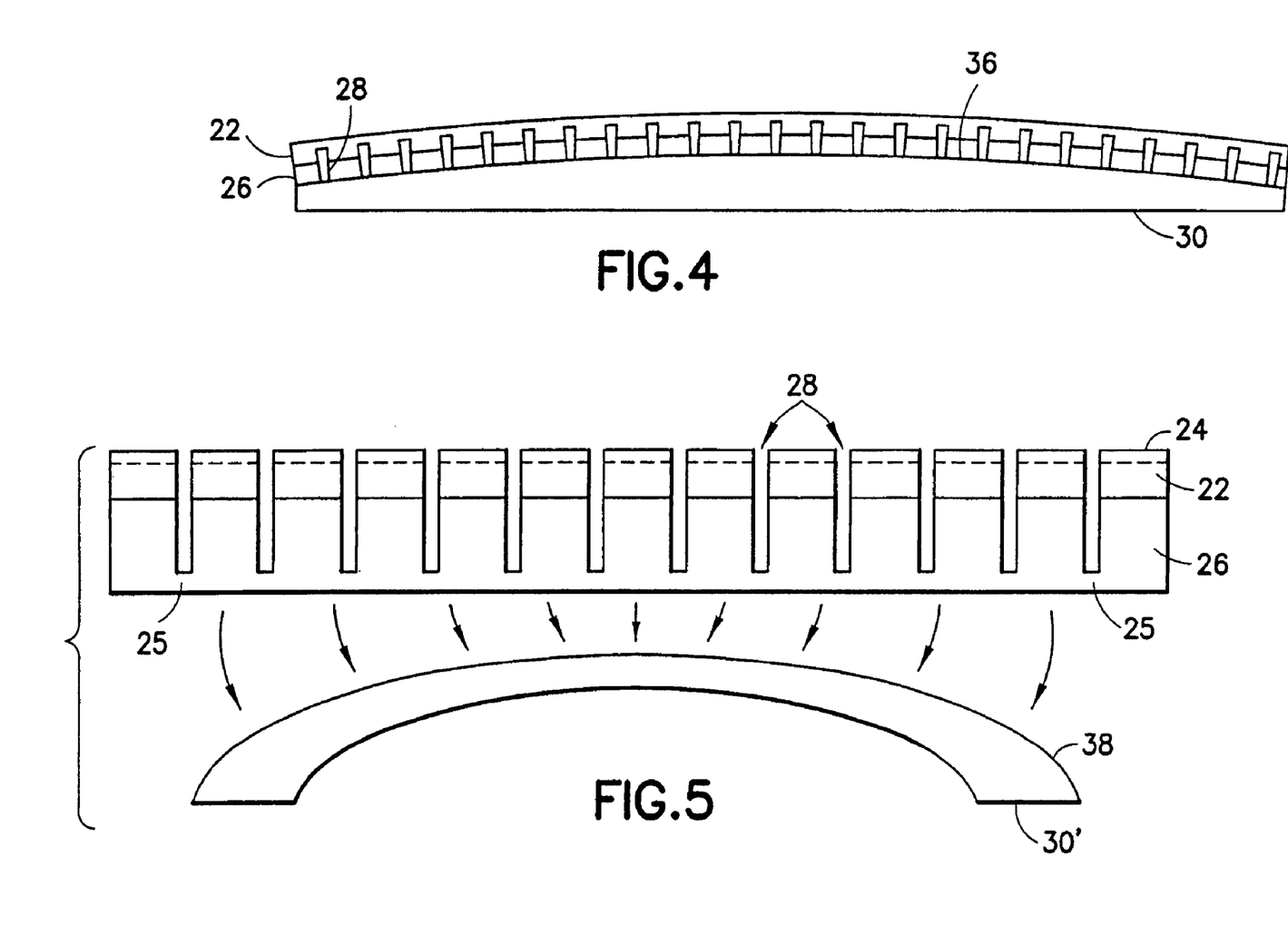
FIG. 4 is a drawing showing a further stage in the manufacturing process wherein the diced lamination shown in FIG. 3 has been bent and attached to a curved support member.
FIG. 5 is a drawing showing a stage in a manufacturing process in accordance with another embodiment of the invention wherein the lamination shown in FIG. 2 has been diced from the front. The arrows indicate the next stage in manufacture wherein the diced lamination is bent and attached to a curved support member.

FIGS. 2 through 4 show three stages in the manufacture of a curved ultrasonic probe in accordance with one embodiment of the invention. In one stage of manufacture, a flat cMUT wafer comprising cMUT cells 24 built on a silicon substrate 22 is laminated, for example, by means of a thin layer of epoxy which would be acoustically transparent (not shown), to a flat backing plate 26 made of acoustically attenuative material. The acoustic backing material has a composition that is acoustically matched to the cMUT substrate 22, to prevent reflection of the acoustic energy back into the device. One example of a suitable backing material comprises a mixture of tungsten and polyvinyl chloride (PVC) powders mixed together and hot pressed in a die as disclosed in U.S. patent application Ser. No. 10/248,022 entitled "Backing Material for Micromachined Ultrasonic Transducer Devices". The backing 26 may be bonded to the back of the silicon substrate 22 using a low-viscosity epoxy after cleaning and application of an adhesion promoter to both surfaces.

The layer 24 demarcated by the dashed line represents a multiplicity of cMUT cells fabricated on the silicon substrate 22. The top surface of cMUT layer 24 forms the front face of the probe. As previously described, groups of cMUT cells are hardwired together to formed respective elements of the transducer probe.

In the next stage of manufacture shown in FIG. 3, the lamination is diced from the rear face of the backing plate 26, forming a multiplicity of generally mutually parallel slots or kerfs 28. Each kerf passes through the entire thickness of the backing plate 26 and through a partial thickness of the silicon substrate 22. The kerfs do not reach the level 24 where the cMUT cells reside, so the cMUT cells are undisturbed by the dicing operation. As a result of the dicing operation, a structure comprising a multiplicity of teeth connected by a compliant spine is formed. Each tooth comprises a layer of silicon and a layer of backing material. The thin webs 25 at the roots of the kerfs 28, which webs are made up of silicon with cMUT cells built thereon, are compliant and allow the lamination to be bent in either forward or backward, bearing in mind however that bending the lamination backward, which narrows the kerfs at the distal ends thereof (i.e., away from the roots), is constrained by the abutment of adjacent teeth on opposite sides of each kerf. Bending in the other direction is not constrained in this manner.

Dicing kerfs or slots used to relieve stresses for bending may occur with a regular spacing, one kerf per element, in which case the kerfs are preferably located at the border between adjacent elements. Typically, elements occur with a pitch on the order of tenths of a millimeter, whereas kerfs or slots for bending may only be necessary with a pitch on the order of a millimeter. The simplest solution would be to use a periodic array of dicing slots, for example every fifth or every tenth element. This leads to a uniform bending of the chip.

FIG. 4 is a drawing showing a further stage in the manufacturing process wherein the diced lamination shown in FIG. 3 has been bent backward and attached to a curved support member 30. More specifically, the webs 25 are all bent in the same direction to form a bowed diced lamination wherein the active front face of the lamination, where the cMUT cells reside, is generally curved. In this case, the widths of the roots of the kerfs 28 are substantially unchanged, while the widths at the opposite ends of the kerfs (between the tips of adjacent teeth) are narrowed somewhat. The end faces of the teeth are attached to a curved front face 36 the support member 30. The curved front face of support member 30 in this example has a curved profile that is constant in the elevational direction of the final probe. Since the lamination bends primarily at the thin webs 25, the cMUT cells will be generally disposed along segments of a faceted surface having a convex profile that approximates a portion of a polygon. The final probe has an increased field of view due to the convexity of the cMUT array.

Alternatively, the lamination shown in FIG. 3 could be bent forward and then attached to a support member having a concave curved front face whose profile is constant in the elevational direction. This will provide a focused ultrasonic probe with the cMUT cells again generally disposed along segments of a faceted surface having a concave profile that approximates a portion of a polygon.

If the silicon webs connecting the teeth of the lamination are sufficiently thin, a probe may be formed with a cMUT array that curves in both the elevational and azimuthal direction. This requires dicing multiple kerfs in two directions for example orthogonal to one another. In this case the web should be sufficiently elastic or deformable. The resulting dish-shaped array may be either convex or concave.

FIG. 5 shows an alternative embodiment of the invention. Instead of dicing from the rear, the lamination is diced from the front, again forming a multiplicity of generally mutually parallel slots or kerfs 28. In this embodiment, each kerf 28 passes through the entire thickness of the silicon substrate 22 and through a partial thickness of the backing plate 26. As a result of the dicing operation, a structure comprising a multiplicity of teeth connected by a compliant spine is formed. Each tooth comprises a layer of silicon and a layer of backing material. In this embodiment, the thin compliant webs 25 at the roots of the kerfs 28 are made of the backing material. These compliant webs allow the lamination to be bent either forward or backward, again bearing in mind however that bending the lamination backward, which narrows the kerfs at the distal ends thereof (i.e., away from the roots), is constrained by the abutment of adjacent teeth on opposite sides of each kerf.

Because the cMUT layer 24 of the wafer is diced, the cMUT cells are built on only those portions of the silicon substrate that will not be diced. For example, the cMUT cells could be micromachined so that a respective element occupies the end face of each tooth. Alternatively, the pitch of the kerfs could be such that each tooth end face is occupied by a respective set of elements. In either case, the cMUT cells are arranged during micromachining such that the areas where kerfs are cut are not occupied by cMUT cells. Otherwise any cMUT cell in the path of the dicing saw would be damaged.

In FIG. 5, the curved arrows are intended to represent bowing of the lamination so that the rear face of the backing layer adopts a concave profile. In the next manufacturing step, the concave rear surface of the backing layer 26 will be attached to the convex front surface 38 of a support member 30'. In this embodiment, the profile of the front face of the support member is again constant in the elevational direction. More specifically, the webs 25 are all bent in the same direction to form a bowed diced lamination wherein the teeth, which carry the cMUT cells, are fanned out slightly. The cMUT cells on the end face of a particular tooth lie along a straight line segment, with all of the segments being disposed generally tangent to a line of curvature at respective points along that line of curvature.

Alternatively, the lamination shown in FIG. 5 could be bent forward and then attached to a support member having a concave curved front face whose profile is constant in the elevational direction. This would again provide a focused ultrasonic probe with the cMUT cells again generally disposed along segments of a faceted surface having a concave profile that approximates a portion of a polygon.

Figure 6:
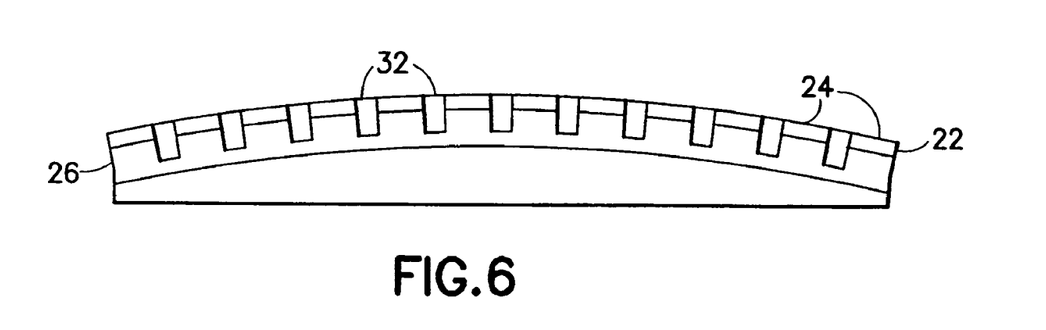
FIG. 6 is a drawing showing a lamination that has been diced from the front and bent, following which the kerfs are filled in with sound-absorbing material.

The embodiment depicted in FIG. 5 raises the possibility of fixed constructive interference from acoustic waves trapped in lateral modes. Since the sides of the dicing slots tend to be good reflectors, sound waves propagating in the lateral direction tend to repeatedly bounce back and forth within the wafer portion of each tooth, to decay slowly, and to leak continuously into the sensing part of the device. It is highly desirable to damp these lateral sound waves by filling the dicing kerfs with attenuating material such as rubberized plastics, or silicones. This kerf-filling material may also be filled with high-density particles (such as tungsten) to match the acoustic impedance of the silicon. This improves the sound energy transfer from the silicon into the attenuating kerf filler and eliminates modes that may arise from periodic slots. This feature is shown in FIG. 6, wherein the acoustically attenuative material filling the kerfs is designated by the numeral 32. Another strategy is to randomize the dicing slots to avoid strict periodicity and hence a strong signal at a specific frequency.

The kerf filling could also be changed to damp out and isolate other signal crossover. For example, thermal insulating material could be put in the kerfs to isolate temperature measurement at each tooth.

Optionally, the cMUT wafer can be thinned before bending by removing a layer of silicon from the back of the wafer. This method seeks to reduce the stresses in the silicon. Typical cMUT wafers are 400-600 microns thick. The wafer can be thinned to provide flexibility (e.g. typically ~150 microns). Afterwards, a backing is applied to form the lamination depicted in FIG. 2. Thinned silicon wafer curls just like a postage stamp.

Figure 7:
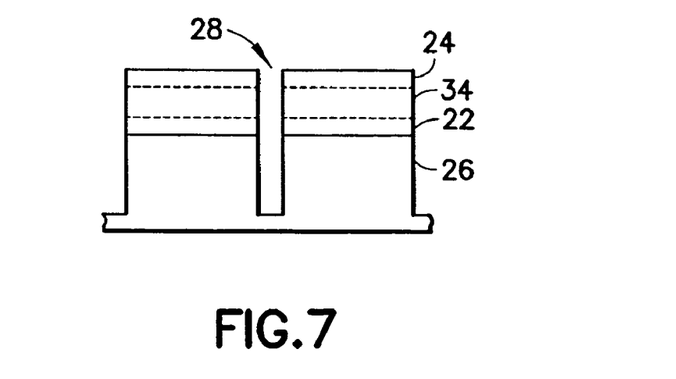
FIG. 7 is a drawing showing two teeth of a diced lamination having CMOS electronics integrated into the cMUT wafer in accordance with a further embodiment of the invention.

In accordance with further aspects of the invention, a high-bandwidth cMUT array can be integrated with switching circuits on a silicon wafer to provide functionality related to or separate from the ultrasound transduction. In such an integrated structure, the size of the transducer elements establishes the dimensions of the switching circuits in the silicon immediately below the elements. Such an integrated structure is generally depicted in FIG. 7 (which shows only two teeth of an array) for the case where a wafer/backing lamination is diced from the front. For example, CMOS electronics 34 are fabricated on the top of the silicon substrate 22. Then the cMUT cells 24 are fabricated on top of the CMOS electronics 34. Because the structure shown in FIG. 7 is diced from the front, the layers containing the cMUT cells 24 and the CMOS electronics 34 are both diced. Accordingly, the cMUT cells and the CMOS electronics are built on only those portions of the silicon substrate that will not be diced, thereby avoiding damage to the cMUTs and the CMOS electronics. The flat backing plate 26 is made of acoustically attenuative material.

The cMUT bottom electrodes (not shown in FIG. 7) can be connected to the CMOS electronics using additional passivation and metal layers (not shown). Electrical interconnect from one layer to another can be provided by metallized vias through the passivation layers (not shown). Some examples of switching circuits can be high-voltage switching transistors, gate-drive transistors for the switches, control logic, impedance matching devices, and other circuitry.

In the case wherein the sensors are bulk micromachined on a substrate, a second substrate containing associated circuitry can be laminated to the sensor substrate and electrically connected via metallized vias in the latter, While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A sensor device comprising:
   a support structure comprising a spine having a profile that is generally curved and a multiplicity of teeth extending from one side of said curved spine; and
   a multiplicity of micromachined sensors supported by said support structure in positions whereby a curved aperture is provided.

2. The device as recited in claim 1, wherein said sensors comprise MUT cells.

3. The device as recited in claim 2, wherein said MUT cells are built on said spine, and said support structure further comprises a support member to which the ends of said teeth are attached.

4. The device as recited in claim 3, wherein the portion of said spine on which said MUT cells are built is made of silicon, as is portions of said teeth contiguous with said spine.

5. The device as recited in claim 2, wherein said MUT cells are built and distributed on the ends of said teeth, and said support structure further comprises a support member to which said spine is attached.

6. The device as recited in claim 5, wherein the portions of said teeth on which said MUT cells are built are made of silicon.

7. The device as recited in claim 1, wherein said curved aperture is convex.

8. The device as recited in claim 1, wherein said curved aperture is concave.

9. The device as recited in claim 1, wherein said teeth have non-periodic spacing.

10. A sensor device comprising:
    a continuous substrate comprising a front face and a multiplicity of spaced plateaus projecting rearward;
    a multiplicity of micromachined sensors fabricated on or in said substrate at its front face;
    a multiplicity of backing bodies, each backing body being attached to a rear face of a respective plateau;
    a support member having a front face, respective rear faces of said backing bodies being attached to said front face of said support member,
    wherein said sensors do not lie in the same plane.

11. The device as recited in claim 10, wherein said sensors comprise MUT cells.

12. The device as recited in claim 10, wherein said front face of said support member has a profile that is generally convex.

13. The device as recited in claim 10, wherein said front face of said support member has a profile that is generally concave.

14. The device as recited in claim 10, further comprising a multiplicity of circuits built on a level below said sensors.

15. The device as recited in claim 14, wherein said circuits comprise CMOS electronics.

16. The device as recited in claim 10, wherein said substrate is made of silicon.

17. The device as recited in claim 11, wherein said MUT cells are cMUT cells.

18. The device as recited in claim 11, wherein said MUT cells are pMUT cells.

19. The device as recited in claim 10, wherein said backing bodies have non-periodic spacing.

20. A sensor device comprising:
a support member having a front face;
a continuous layer of backing material comprising a rear face attached to said front face of said support member;
a multiplicity of backing bodies connected to and extending forward of said continuous layer of backing material;
a multiplicity of sections of a substrate, each substrate section comprising a rear face attached to a front face of a respective backing body, adjacent ones of said substrate sections being separated from each other by a respective acoustically isolating gap or filled space; and
a multiplicity of groups of sensors distributed over the front faces of said substrate sections, each group being built on a front face of a respective one of said substrate sections,
wherein said sensors do not lie in the same plane.

21. The device as recited in claim 20, wherein said sensors comprise MUT cells.

22. The device as recited in claim 20, wherein said front face of said support member has a profile that is generally convex.

23. The device as recited in claim 20, wherein said front face of said support member has a profile that is generally concave.

24. The device as recited in claim 20, further comprising a multiplicity of circuits distributed in said substrate sections on a level below said sensors.

25. The device as recited in claim 24, wherein said circuits comprise CMOS electronics.

26. The device as recited in claim 20, wherein said substrate sections are made of silicon.

27. The device as recited in claim 21, wherein said MUT cells are cMUT cells.

28. The device as recited in claim 21, wherein said MUT cells are pMUT cells.

* * * * *